United States Patent
Gerety

(10) Patent No.: US 9,835,604 B2
(45) Date of Patent: Dec. 5, 2017

(54) TEMPERATURE COMPENSATION OF GAS SENSORS

(71) Applicant: KONINKLIJKE PHILIPS N.V., Eindhoven (NL)

(72) Inventor: Eugene Peter Gerety, Seymour, CT (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/304,216

(22) PCT Filed: Apr. 2, 2015

(86) PCT No.: PCT/IB2015/052416
§ 371 (c)(1),
(2) Date: Oct. 14, 2016

(87) PCT Pub. No.: WO2015/159176
PCT Pub. Date: Oct. 22, 2015

(65) Prior Publication Data
US 2017/0038354 A1    Feb. 9, 2017

Related U.S. Application Data

(60) Provisional application No. 61/979,315, filed on Apr. 14, 2014.

(51) Int. Cl.
*G01N 33/00* (2006.01)
*G01N 21/3504* (2014.01)
*G01N 21/31* (2006.01)

(52) U.S. Cl.
CPC ......... *G01N 33/0006* (2013.01); *G01N 21/31* (2013.01); *G01N 21/3504* (2013.01); *G01N 33/004* (2013.01); *G01N 2201/1211* (2013.01)

(58) Field of Classification Search
CPC ........... G01N 33/0006; G01N 21/3504; G01N 2201/1211; G01N 33/004
See application file for complete search history.

(56) References Cited

U.S. PATENT DOCUMENTS 5,838,008 A * 11/1998 Esler .................. G01J 3/28
250/339.07
6,087,182 A * 7/2000 Jeng ...................... G01N 21/05
356/72

(Continued)

*Primary Examiner* — Jewel V Thompson

(57) ABSTRACT

A target gas sensor employing a radiation source (20) and a radiation sensor (30) including a reference radiation detector (31), a target radiation detector (32), a temperature sensor (34), a temperature controller (35) and a target gas detection processor (37). In operation, radiation source (20) controls a propagation of radiation (RAD) through a gas mixture (GM) contained by an airway (10) to radiation sensor (30). Reference radiation detector (31) generates a reference detection signal (RD) indicative of a detected magnitude of a reference wavelength ($\lambda_{REF}$) of the radiation, and target radiation detector (32) generates a target detection signal (TD) indicative of a detected magnitude of a target wavelength ($\lambda_{TG}$) of the radiation. Temperature sensor (34) senses a temperature of radiation detectors (31, 32) whereby temperature controller (35) regulates a heating of the radiation detectors (31, 32) relative to a regulated detector temperature ($T_{REG}$). Target gas detection processor (37) measures the target gas concentration within the sample of the gas mixture (GM) as a function of an absorbing spectral response ratio ($SRR_A$) and a temperature compensation (TPC).

20 Claims, 4 Drawing Sheets

(56) References Cited

U.S. PATENT DOCUMENTS

| | | |
|---|---|---|
| 6,218,665 B1 | 4/2001 | Yamamori et al. |
| 7,372,573 B2 * | 5/2008 | Spartz .................. G01N 21/031 356/451 |
| 8,155,890 B2 * | 4/2012 | Goto .................. G01N 21/3504 250/339.13 |
| 9,228,989 B2 | 1/2016 | Gerety et al. |
| 9,651,488 B2 * | 5/2017 | Scherer .................. G01N 21/61 |
| 2006/0145078 A1 | 7/2006 | Russell |
| 2017/0010207 A1 * | 1/2017 | Fetzner .............. G01N 21/3504 |

* cited by examiner

TEMPERATURE COMPENSATION OF GAS SENSORS

This application is a national stage application under 35 U.S.C. §371 of International Application No. PCT/IB2015/052416 filed on Apr. 2, 2015 and published in the English language on Oct. 22, 2015 as International Publication No. WO2015/159176, which claims priority to U.S. Application No. 61/979,315 filed on Apr. 14, 2014, the entire disclosures of which are incorporated herein by reference.

The present invention generally relates to gas sensors for measuring a target gas concentration within a sample of a gas mixture based on absorption spectroscopy, in particular capnometers for measuring a carbon dioxide ("CO2") concentration within a sample of a gas mixture based on absorption spectroscopy. The present invention specifically relates to addressing a significant temperature dependency of spectral responses by radiation detectors (e.g., lead selenide ("PbSe") based radiation detectors) employed by gas sensors for measuring the target gas concentration within the gas mixture.

As known in the art, a radiation detector is any device for converting electromagnetic radiation into an electrical signal. Many types of radiation detectors have a temperature-dependent spectral response, and gas sensors employ such radiation detectors to implement an absorption spectroscopy for measuring a concentration of a specific target gas within a sample of a gas mixture.

For example, FIG. 1 illustrates an airway 10 (e.g., a respiratory tube) having a pair of optically transmissive windows 11 and 12 longitudinally aligned with a radiation source (e.g., an infrared emitter and lens) and a radiation sensor 30 having a reference radiation detector 31 and a target radiation detector 32. Radiation source 20 controls a propagation of a radiation RAD through a gas mixture GM contained within airway 10 to radiation sensor 30, which employs components (not shown) for filtering and focusing a reference wavelength $\lambda_{REF}$ of radiation RAD to reference radiation detector 31 and for filtering and focusing a target gas wavelength $\lambda_{TG}$ of radiation RAD to target radiation detector 32. Reference radiation detector 31 converts the filtered and focused radiation RAD into an electric signal having a magnitude representative of a non-absorption by gas mixture GM of radiation RAD at reference wavelength $\lambda_{REF}$, and target radiation detector 32 converts radiation RAD into an electric signal having a magnitude representative of any absorption by the target gas of radiation RAD at target gas wavelength $\lambda_{TG}$.

Gas mixture GM may be a non-absorbing gas mixture which is substantially non-absorbent of radiation RAD at both reference wavelength $\lambda_{REF}$ and the target gas wavelength $\lambda_{TG}$. For example, with CO2 as the target gas, nitrogen gas is suitable to serve as a non-absorbing gas mixture that is substantially non-absorbent of radiation RAD at both reference wavelength $\lambda_{REF}$ and the target gas wavelength $\lambda_{TG}$ for CO2.

Alternatively, gas mixture GM may be an absorbing gas mixture, which is substantially non-absorbent of radiation RAD at reference wavelength $\lambda_{REF}$ and absorbent of radiation RAD at target gas wavelength $\lambda_{TG}$ in dependency on a concentration of the target gas within gas mixture GM.

However, irrespective of whether gas mixture GM is absorbing or non-absorbing, radiation detectors 31 and 32 exhibit a significant temperature dependency, both in the magnitude of their response and in their spectral sensitivity, that must be addressed to accurately measure a target gas concentration within gas mixture GM.

More particularly, for detecting CO2 as the target gas within the sample of a non-absorbing gas mixture with radiation detectors 31 and 32 being PbSe based radiation detectors, FIG. 2 illustrates reference wavelength $\lambda_{REF}$ of infrared radiation at 3.681 μm and target gas wavelength $\lambda_{TG}$ of infrared radiation at 4.275 μm as plotted against five (5) exemplary temperature response curves of the spectral response of the PbSe based radiation detector at five (5) different temperatures ranging from −45° C. to +45° C. As the shapes of these curves demonstrate, both the magnitude of the response and a peak-sensitivity wavelength of the PbSe based radiation detector depend heavily on temperature. At −45° C., for example, the overall magnitude of the response curve of the PbSe based radiation detector is approximately three (3) times greater than it is at +45° C., and the peak response wavelength is longer (about 4.7 μm at −45° C. vs. about 3.9 μm at +45° C.). Of importance to note is how the response of the PbSe based radiation detector varies with temperature reference wavelength $\lambda_{REF}$ of infrared radiation at 3.681 μm and target gas wavelength $\lambda_{TG}$ of infrared radiation at 4.275 μm.

Referring back to FIG. 1, to address the temperature dependency of radiation detectors 31 and 32, it is known in the art to implement a temperature regulation of radiation detectors 31 and 32 for purpose of "locking" the radiation detectors 31 and 32 to a fixed temperature whereby the responses of radiation detectors 31 and 32 is also "locked" to thereby obtain stable, repeatable responses by radiation detectors 31 and 32. To this end, FIG. 3 illustrates a heater 33, a temperature sensor 34, a temperature controller 35 and a target gas detection processor 36.

In operation, referring to FIGS. 1 and 2, radiation source 20 (FIG. 1) controls a propagation of a 100 Hz modulated infrared radiation RAD through gas mixture GM contained by airway 10 to radiation sensor 30 whereby reference wavelength $\lambda_{REF}$ of radiation RAD is filtered and focused to reference radiation detector 31 and target gas wavelength $\lambda_{TG}$ of radiation RAD is filtered and focused to target radiation detector 32. Accordingly, a magnitude of a reference detection signal RD generated by reference radiation detector 31 represents a non-absorption by gas mixture GM of radiation RAD at reference wavelength $\lambda_{REF}$, and a magnitude of a target detection signal TD generated by target radiation detector 32 represents any absorption by the target gas of radiation RAD at target gas wavelength $\lambda_{TG}$.

Temperature sensor 34 generates a detector temperature signal DT indicative of a temperature of radiation detectors 31 and 32, and responsive to detector temperature signal DT, temperature controller 35 regulates a heating of radiation detectors 31 and 32 via heater 33. As shown in FIG. 4, a temperature plot of reference detection signal RD and target detection signal TD derived from the non-absorbing temperature curves of FIG. 2 yields a reference detection signal $RD_{NR}$ and a target detection signal $TD_{NR}$ at a regulated detector temperature $T_{REG}$ (e.g., 50° C.±2° C.). Processor 36 computes a regulated spectral response ratio $SRR_{NR}$ equal to $TD_{NR}/RD_{NR}$ or the inverse thereof as a baseline for measuring a target gas concentration of a sample of an absorbing gas mixture GM.

Specifically, subsequent to radiation RAD passing through absorbing gas mixture GM, a reference detection signal $RD_A$ and a target detection signal $TD_A$ are sampled to yield absorbing spectral response ratio $SRR_A$ equal to $TD_A/RD_A$ or the inverse thereof. Ratios $SRR_{NR}$ and $SRR_A$ are compared whereby any differential between ratios $SRR_{NR}$ and $SRR_A$ is an indication of absorption by the target gas (e.g., CO2) of radiation RAD that may be mathematically processed as known in the art to measure the target gas concentration.

While the temperature regulation of detectors 31 and 32 provide stable, repeatable responses for temperatures equal to or below the regulated temperature, for instances where the temperatures of detectors 31 and 32 exceed the regulated temperature due to ambient temperature and/or other factors, the temperature dependent responses of detectors 31 and 32 preclude any measurements of the target gas concentration at the unregulated high temperatures.

To address the unregulated high temperatures, the present invention provides a temperature compensation technique for measuring a target gas concentration within a sample of absorbing gas mixture at unregulated high temperatures.

One form of the present invention is a gas sensor employing a radiation source and a radiation sensor for propagating radiation from the radiation source through a gas mixture contained by an airway to the radiation sensor. The radiation sensor includes a reference radiation detector (e.g., a PbSe radiation detector), a target radiation detector (e.g., a PbSe radiation detector), a temperature sensor (e.g., a thermistor), a temperature controller, and a temperature compensation based target gas detection processor.

In operation, the reference radiation detector generates a reference detection signal indicative of a detected magnitude of a reference wavelength of the radiation, and the target radiation detector generates a target detection signal indicative of a detected magnitude of a target wavelength of the radiation. The magnitude of the reference wavelength of the radiation represents a non-absorption by the gas mixture of the radiation at the reference wavelength, and the magnitude of the target wavelength of the radiation represents any absorption by the target gas of the radiation at the target wavelength.

The temperature sensor generates a detector temperature signal indicative of a temperature of the radiation detectors, and responsive to the detector temperature signal, the temperature controller regulates a heating of the radiation detectors. Response to the detection signals and the temperature signal, the target gas detection processor measures the concentration of the target gas within the sample of the gas mixture as a function of an absorbing spectral response ratio and a temperature compensation.

In a presence of an absorbing gas mixture contained by the airway, the absorbing spectral response ratio represents a comparison of the target detection signal relative to the reference detection signal at an unregulated detector temperature exceeding the regulated detector temperature.

In a presence of a non-absorbing gas mixture contained by the airway, the temperature compensation is a function of a calibration of a non-absorbing spectral response ratio representative of a comparison of the target detection signal relative to the reference detection signal at the unregulated detector temperature to a regulated spectral response ratio representative of a comparison of the target detection signal relative to the reference detection signal at the regulated detector temperature.

A second form of the present invention is gas sensing device employing the aforementioned gas sensor and the airway The airway may have optically transmissive windows longitudinally aligned with the radiation source and the radiation sensor to facilitate the propagation of the radiation from the radiation source through the gas mixture contained by the airway to the radiation sensor.

A third form of the present invention is method of operating the aforementioned gas sensor. The method involves:

(1) the radiation source controlling a propagation of radiation through a non-absorbing gas mixture contained by an airway, (2) the reference radiation detector generating a reference detection signal indicative of a detected magnitude of a reference wavelength of the radiation, (3) the target radiation detector generating a target detection signal indicative of a detected magnitude of a target wavelength of the radiation, (4) the temperature sensor generating a detector temperature signal indicative of a temperature of the radiation detectors, (5) responsive to the detector temperature signal, the temperature controller regulating a heating of the radiation detectors relative to a regulated detector temperature, and (6) responsive to the signals in the presence of non-absorbing gas mixture contained by airway, the target gas detection processor computing a temperature compensation as a function of a calibration of a non-absorbing spectral response ratio representative of a comparison of the target detection signal relative to the reference detection signal at an unregulated detector temperature exceeding the regulated detector temperature to a regulated spectral response ratio representative of a comparison of the target detection signal relative to the reference detection signal at the regulated detector temperature.

The method further involves:

(7) the radiation source controlling a propagation of a radiation through an absorbing gas mixture contained by the airway, and (8) responsive to the signals in the presence of the absorbing gas mixture contained by airway, the target gas detection processor computing an absorbing spectral response ratio representative of a comparison of the target detection signal relative to the reference detection signal at the unregulated detector temperature.

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

For purposes of the present invention, the terms "radiation", "gas mixture", "non-absorbing", "absorbing", "radiation detector", "sensor", "controller" and "processor" and as well as synonymous and related terms are to be broadly interpreted as known in the art of the present invention.

Figure 5:
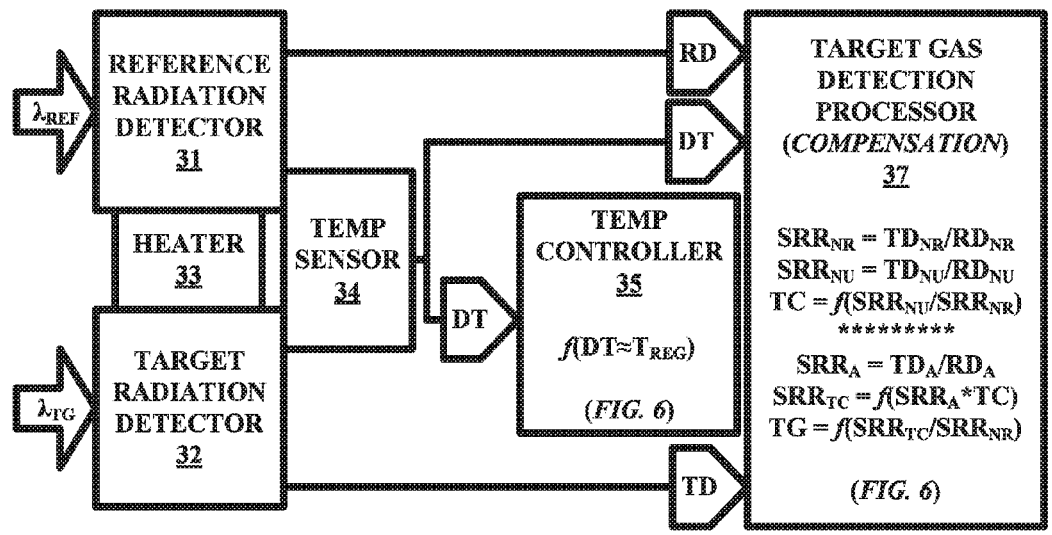
FIG. 5 illustrates a block diagram of an exemplary embodiment of a radiation sensor in accordance with the present invention.

To facilitate an understanding of the present invention, exemplary embodiments of the present invention will be provided herein directed a target gas detection processor 37 as shown in FIG. 5 for implementing a temperature compensation technique for measuring a target gas concentration within a sample of absorbing gas mixture at unregulated high temperatures. In practice, target gas detection processor 37 employs hardware, software, firmware, and/or circuitry as required to implement a particularly embodiment of the temperature compensation technique of the present invention.

Figure 7:
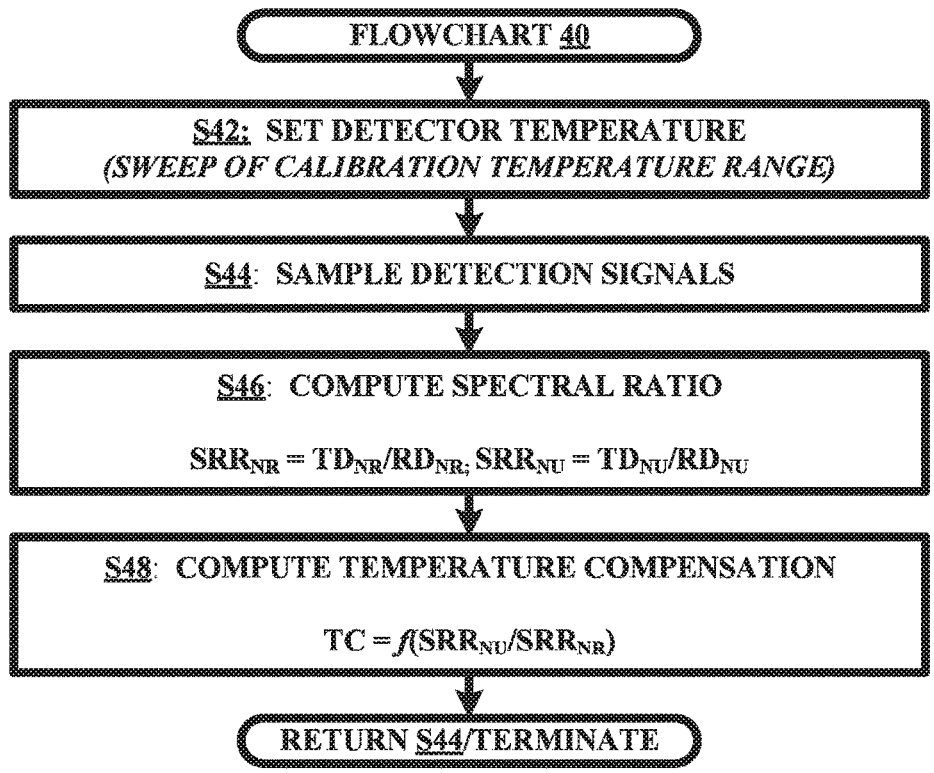
FIG. 7 illustrates a flowchart representative of an exemplary embodiment of a temperature compensation computation method in accordance with the present invention.
Figure 8:
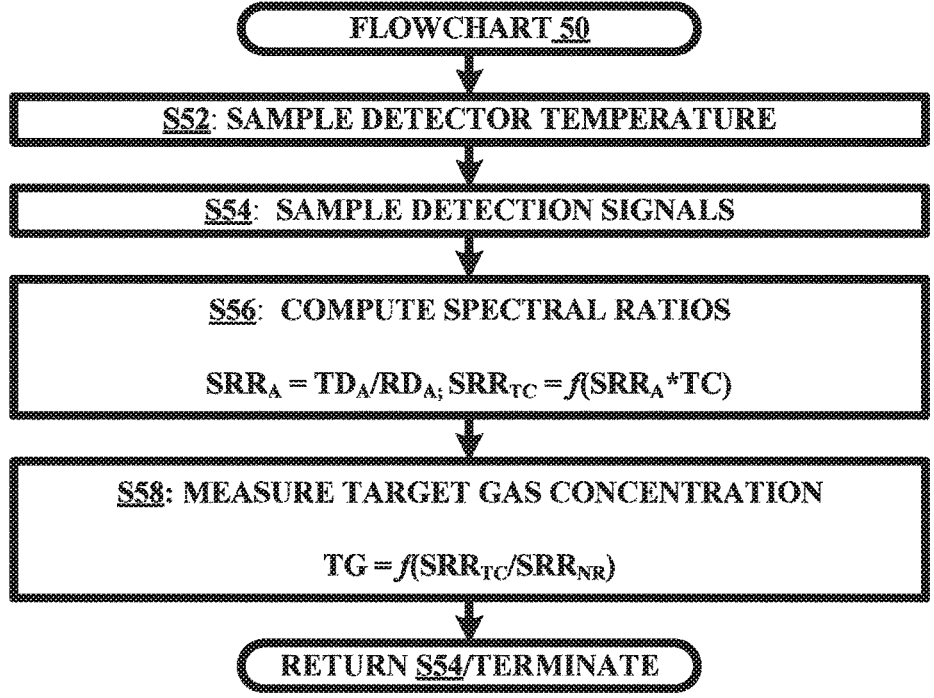
FIG. 8 illustrates a flowchart representative of an exemplary embodiment of a temperature compensation measurement method in accordance with the present invention.

In one embodiment of target gas detection processor 37, software modules are installed on processor 37 for executing a temperature compensation computation method of the present invention represented by a flowchart 40 as shown in FIG. 7 and a temperature compensation measurement method of the present invention represented by a flowchart 50 as shown in FIG. 8.

Figure 1:
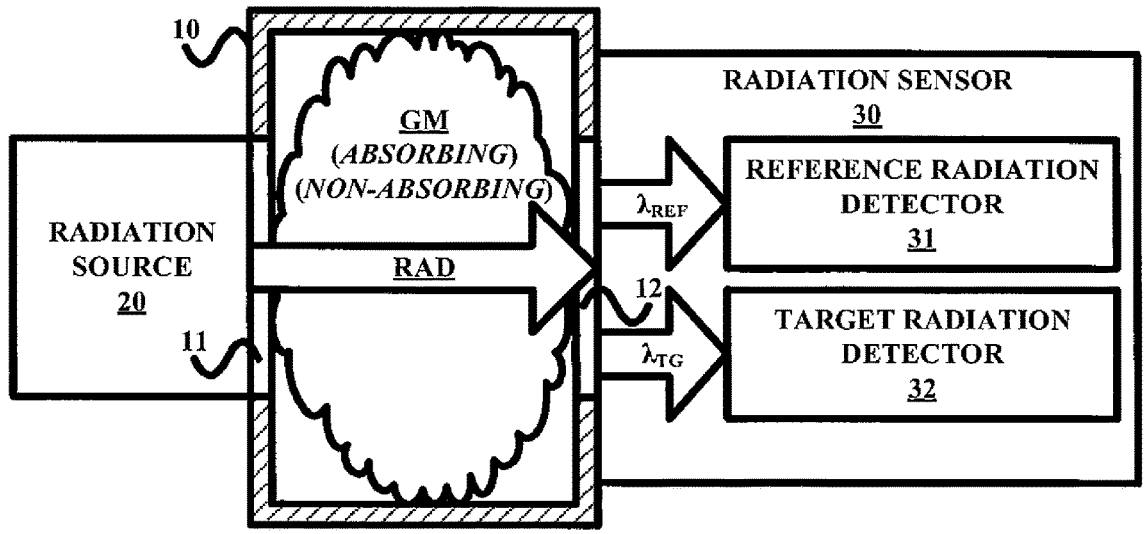
FIG. 1 illustrates a block diagram of an exemplary gas sensing device as known in the art.
Figure 2:
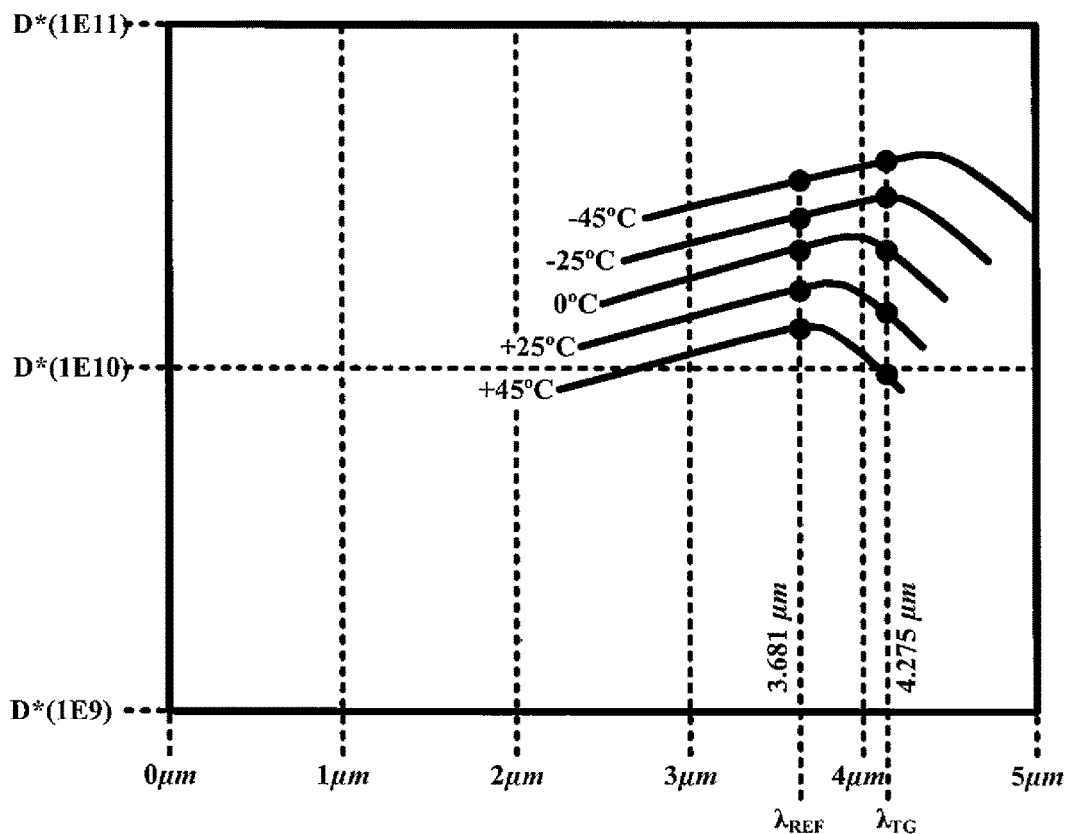
FIG. 2 illustrates a graphical representation of exemplary temperature spectral responses of a radiation detector at various temperatures as known in the art.
Figure 3:
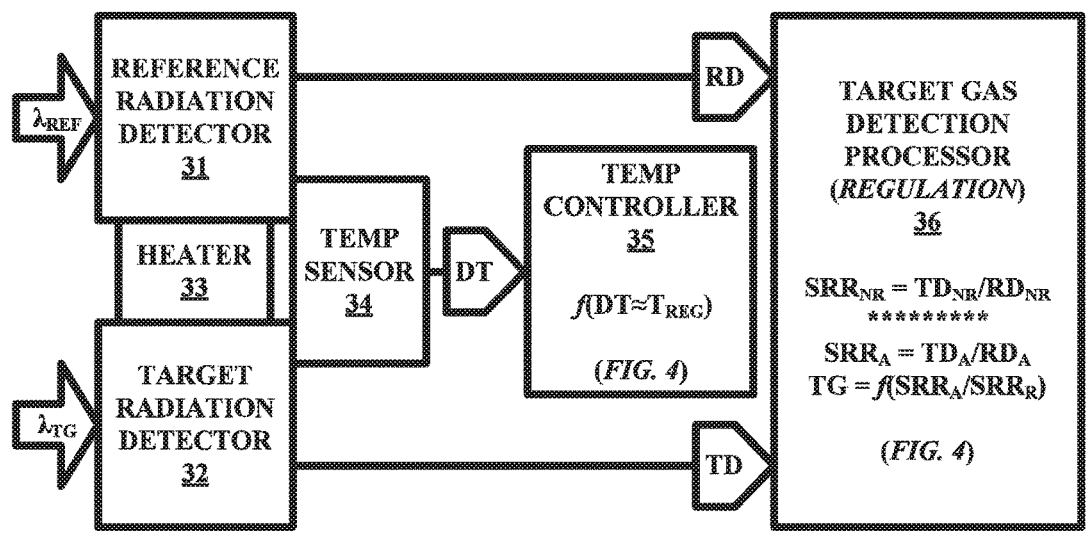
FIG. 3 illustrates a block diagram of an exemplary radiation sensor as known in the art.
Figure 4:
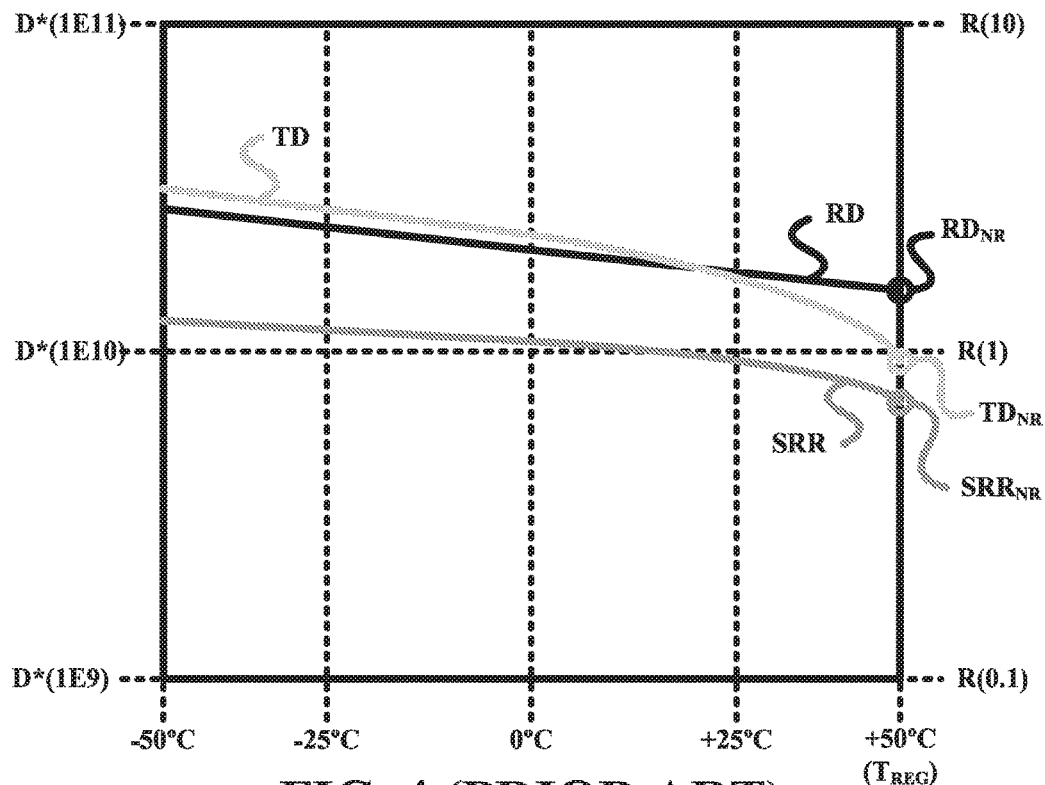
FIG. 4 illustrates a graphical representation of an exemplary spectral response ratio of a radiation detector utilized by the radiation sensor illustrated in FIG. 3 as known in the art.
Figure 6:
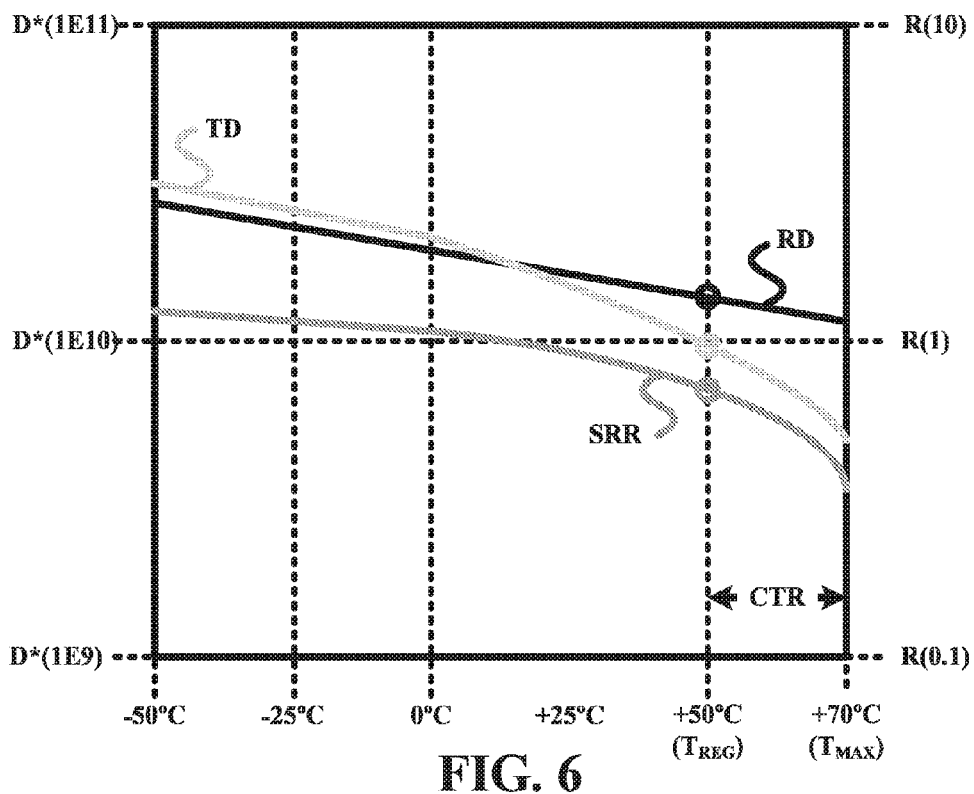
FIG. 6 illustrates a graphical representation of an exemplary spectral response ratio of a radiation detector utilized by the radiation sensor illustrated in FIG. 5 as known in the art.

Referring to FIGS. 5-7, flowchart 40 is initiated subsequent to airway 10 (FIG. 1) being "zeroed" by a non-absorbing gas mixture (e.g., nitrogen for COS as the target gas) and radiation source 20 (FIG. 1) controlling a propagation of radiation RAD through the non-absorbing gas mixture to detectors 31 and 32. In one embodiment, the radiation is a 100 Hz modulated infrared radiation having a temperature peak of 600° C. and a temperature valley of 485° C.

Stages S42-S46 of flowchart 40 involve a temperature sweep over a calibrated temperature range CTR between a regulated temperature $T_{REG}$ (e.g., 50° C. as exemplary shown in FIG. 6) and a maximum expected temperature $T_{MAX}$ (e.g., 70° C. as exemplary shown in FIG. 6). The temperature sweep may commence at either end of the calibrated temperature range CTR and thereafter proceed in fixed intervals to the other end of the calibrated temperature range CTR.

According, stage S42 of flowchart 40 encompasses processor 37 requesting a specific detector temperature DT, which is set by temperature controller 35, and a stage S44 of flowchart 40 encompasses processor 37 sampling detection signals RD and TD. In practice, processor 37 may be synchronized with radiation source 20 to sample detections signals RD and TD at either the temperature peaks and/or temperature valleys of radiation RAD during stage S44 of flowchart 40.

If the temperature is the regulated detector temperature, then processor 37 during stage S46 of flowchart 40 computes a regulated spectral response ratio $SRR_{NR}$ equal to $TD_{NR}/RD_{NR}$ or the inverse thereof.

If the temperature is an unregulated detector temperature, then processor 37 during stage S46 computes a non-absorbing spectral response ratio $SRR_{NU}$ equal to $TD_{NU}/RD_{NU}$ or the inverse thereof.

Upon completion of the temperature sweep of stages S42-S44 or after each execution of stage S46, stage S48 of flowchart 50 encompasses processor 37 computing a temperature compensation TC derived from the computed spectral response ratios SRR.

In one embodiment of stage S48, each spectral response ratio SRR vs. temperature in saved in a table. Regulated spectral response ratio $SRR_{NR}$ is used for each temperature of the table to compute a temperature compensation correction factor equal to $SRR_{NR}/SRR_{NU}$. Each correction factor is stored in the table for lookup during a stage S56 of flowchart 50 as subsequently described herein.

In an alternative embodiment of stage S48, instead of creating a table, a "best fit" polynomial function or any other suitable type of mathematical function is created to relate a single correction factor to temperature to be used during stage S56 of flowchart 50.

Referring to FIGS. 5, 6 and 8, flowchart 50 is initiated subsequent to airway 10 (FIG. 1) containing an absorbing gas mixture (e.g., respiratory gas with COS as the target gas).

A stage S52 of flowchart 50 encompasses radiation source 20 (FIG. 1) emitting radiation RAD through the absorbing gas mixture to detectors 31 and 32, and radiation source 20 (FIG. 1) controlling a propagation of radiation RAD through the absorbing gas mixture to detectors 31 and 32. Again, the radiation may be 100 Hz modulated infrared radiation having a temperature peak of 600° C. and a temperature valley of 485° C.

A stage S52 of flowchart 50 encompasses processor 37 sampling detector temperature DT and a stage S54 of flowchart 50 encompasses process 37 sampling detection signals RD and TD.

A stage S56 of flowchart 50 encompasses processor 37 computing absorbing spectral ratio $SRR_A$ equal to TDA/RDA or the inverse thereof and computing temperature compensated spectral ratio $SRR_{TC}$ equal to $(TD_A/RD_A)*TC$ or the inverse thereof whereby TC may be a correction factor or derived from polynomial function associated with the detector temperature.

A stage S58 of flowchart 50 encompasses processor 37 comparing ratios $SRR_{NR}$ and $SRR_{TC}$ whereby any differential between ratios $SRR_{NR}$ and $SRR_{TC}$ is an indication of absorption by the target gas (e.g., CO2) of radiation RAD that may be mathematically processed as known in the art to measure the target gas concentration TG.

A stage S56 of flowchart 50 encompasses processor 37 identifying the temperature compensation as associated with the detector temperature to thereby compute a spectral response ratio $SRR_{TC}$ equal to $(TD_A/RD_A)*TC$ or the inverse thereof whereby TC may be a correction factor or derived from polynomial function. Ratios $SRR_{NR}$ and $SRR_{TC}$ are compared whereby any differential between ratios $SRR_{NR}$ and $SRR_{TC}$ is an indication of absorption by the target gas (e.g., CO2) of radiation RAD that may be mathematically processed as known in the art to measure the target gas concentration TG.

Referring to FIGS. 1-8, those having ordinary skill in the art will appreciate numerous benefits of the present invention including, but not limited to, a stable, repeatable response by radiation detectors above a regulated temperature up to a maximum expected temperature of the detectors.

While various embodiments of the present invention have been illustrated and described, it will be understood by those skilled in the art that the embodiments of the present invention as described herein are illustrative, and various changes and modifications may be made and equivalents may be substituted for elements thereof without departing from the true scope of the present invention. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:

1. A target gas sensor for measuring a target concentration within a sample of a gas mixture contained by an airway, the target gas sensor comprising:
   a radiation source and a radiation sensor operable in optical communication with the airway to propagate radiation (RAD) from the radiation source through the gas mixture (GM) contained by the airway to the radiation sensor; and
   wherein the radiation sensor includes
      a reference radiation detector operable to generate a reference detection signal (RD) indicative of a magnitude of a detection signal of the reference radiation detector at a reference wavelength ($\lambda_{REF}$) of the radiation (RAD),
      a target radiation detector operable to generate a target detection signal (TD) indicative of a magnitude of a detection signal of the target radiation detector at a target wavelength ($\lambda_{TG}$) of the radiation (RAD),
      a temperature sensor in thermal communication with the reference radiation detector and the target radiation detector to generate a detector temperature signal (DT) indicative of a temperature of the reference radiation detector and the target radiation detector,
      a temperature controller operable in signal communication with the temperature sensor to regulate a heating of the reference radiation detector and the target radiation detector relative to a regulated detector temperature ($\lambda_{REF}$), wherein the reference radiation detector and the target radiation detector are maintained at the regulated detector temperature ($T_{REG}$) by heating alone when the ambient temperature lies within a suitable range, and
      a target gas detection processor operable in signal communication with the reference radiation detector, the target radiation detector and the temperature sensor to measure the target gas concentration within the sample of the gas mixture (GM) as a function of an absorbing spectral response ratio ($SRR_A$) and a temperature compensation factor (TPC), wherein a spectral response ratio is a ratio of a target detector signal to a reference detector signal,
      wherein, in a presence of an absorbing gas mixture contained by airway, the absorbing spectral response ratio ($SRR_A$) represents a comparison of the target detection signal ($TD_A$) relative to the reference detection signal ($RD_A$) at an unregulated detector temperature exceeding the regulated detector temperature ($T_{REG}$), and
      wherein, in a presence of a non-absorbing gas mixture contained by airway, the temperature compensation factor (TPC), which is a predetermined function of temperature representing a calibration of a non-absorbing spectral response ratio ($SRR_{NU}$) representative of a comparison of the target detection signal ($TD_{NU}$) relative to the reference detection signal ($RD_{NU}$) at the unregulated detector temperature to a regulated spectral response ratio ($SRR_{NR}$) representative of a comparison of the target detection signal ($TD_{NR}$) relative to the reference detection signal ($RD_{NR}$) at the regulated detector temperature ($T_{REG}$) determined in the presence of a non-absorbing gas.

2. The target gas sensor of claim 1, wherein the target gas detection processor is operable to compute a temperature compensated spectral response ratio ($SRR_{TC}$) as a result of an application of the temperature compensation factor (TPC) to the absorbing spectral response ratio ($SRR_A$).

3. The target gas sensor of claim 2, wherein the target gas detection processor is further operable to compare the temperature compensated spectral response ratio ($SRR_{TC}$) to the regulated spectral response ratio ($SRR_{NR}$).

4. The target gas sensor of claim 1, wherein the target gas is carbon dioxide ($CO_2$).

5. The target gas sensor of claim 4, wherein the absorbing gas mixture (GMA) is a respiratory gas.

6. The target gas sensor of claim 1, wherein the reference radiation detector and the target radiation detector are lead selenide PbSe based radiation detectors.

7. The target gas sensor of claim 1, wherein the temperature sensor is a thermistor thermally coupled to the reference radiation detector and the target radiation detector.

8. A target gas sensing device, comprising:
   an airway operable to contain a gas mixture (GM);
   a radiation source and a radiation sensor operable in optical communication with the airway to propagate radiation (RAD) from the radiation source through the gas mixture (GM) contained by the airway to the radiation sensor; and
   wherein the radiation sensor includes
      a reference radiation detector operable to generate a reference detection signal (RD) indicative of a magnitude of a detection signal of the reference radiation detector at a reference wavelength ($\lambda_{REF}$) of the radiation (RAD),
      a target radiation detector operable to generate a target detection signal (TD) indicative of a magnitude of a detection signal of the target radiation detector at a target wavelength ($\lambda_{TG}$) of the radiation (RAD),
      a temperature sensor in thermal communication with the reference radiation detector and the target radiation detector to generate a detector temperature signal (DT) indicative of a temperature of the reference radiation detector and the target radiation detector,
      a temperature controller operable in signal communication with the temperature sensor to regulate a heating of the reference radiation detector and the target radiation detector relative to a regulated detector temperature ($T_{REG}$), wherein the reference radiation detector and the target radiation detector are maintained at the regulated detector temperature ($T_{REG}$) by heating alone when the ambient temperature lies within a suitable range, and
      a target gas detection processor operable in signal communication with the reference radiation detector, the target radiation detector and the temperature sensor to measure the concentration of the target gas within the sample of the gas mixture (GM) as a function of an absorbing spectral response ratio ($SRR_A$) and a temperature compensation factor (TPC), wherein a spectral response ratio is a ratio of a target detector signal to a reference detector signal,
      wherein, in a presence of an absorbing gas mixture (GMA) contained by airway, the absorbing spectral response ratio ($SRR_A$) represents a comparison of the target detection signal ($TD_A$) relative to the reference detection signal ($RD_A$) at an unregulated detector temperature exceeding the regulated detector temperature ($T_{REG}$), and wherein, in a presence of a non-absorbing gas mixture (GMN) contained by airway, the temperature compensation factor (TPC), which is a predetermined function of temperature representing a calibration of a non-absorbing spectral response ratio ($SRR_{NU}$) representative of a comparison of the target detection signal ($TD_{NU}$) relative to the reference detection signal ($RD_{NU}$) at the unregulated detector temperature to a regulated spectral response ratio ($SRR_{NR}$) representative of a comparison of the target detection signal ($TD_{NR}$) relative to the reference detection signal ($RD_{NR}$) at the regulated detector temperature ($T_{REG}$) determined in the presence of a non-absorbing gas.

9. The target gas sensing device of claim 8, wherein the target gas detection processor is further operable to compute the temperature compensated spectral response ratio ($SRR_{TC}$) as a result of an application of the temperature compensation (TPC) to the absorbing spectral response ratio ($SRR_A$).

10. The target gas sensing device of claim 9, wherein the target gas detection processor is further operable to compare the temperature compensated spectral response ratio ($SRR_{TC}$) to the regulated spectral response ratio ($SRR_{NR}$).

11. The target gas sensing device of claim 8, wherein the target gas is carbon dioxide ($CO_2$).

12. The target gas sensing device of claim 11, wherein the absorbing gas mixture (GMA) is a respiratory gas.

13. The target gas sensing device of claim 8, wherein the reference radiation detector and the target radiation detector are lead selenide PbSe based radiation detectors.

14. The target gas sensing device of claim 8, wherein the temperature sensor is a thermistor thermally coupled to the reference radiation detector and the target radiation detector.

15. The target gas sensing device of claim 1, wherein the airway includes a pair of optically transmissive windows longitudinally aligned with the radiation source and the radiation sensor to establish the optical communication between the radiation source and the radiation sensor.

16. A method of operating a target gas sensor employing a radiation source and a radiation sensor including a reference radiation detector, a target radiation detector, a temperature sensor, a temperature controller, and a target gas detection processor, the method comprising:

the radiation source controlling a propagation of a radiation (RAD) through a non-absorbing gas mixture (GMN) contained by an airway;

the reference radiation detector generating a reference detection signal (RD) indicative of a magnitude of a detection signal of the reference radiation detector at a reference wavelength ($\lambda_{REF}$) of the radiation (RAD);

the target radiation detector generating a target detection signal (TD) indicative of a magnitude of a detection signal of the target radiation detector at a target wavelength ($\lambda_{TG}$) of the radiation (RAD);

the temperature sensor generating a detector temperature signal (DT) indicative of a temperature of the reference radiation detector and the target radiation detector;

responsive to the detector temperature signal (DT), the temperature controller regulating a heating of the reference radiation detector and the target radiation detector relative to a regulated detector temperature ($T_{REG}$), wherein the reference radiation detector and the target radiation detector are maintained at the regulated detector temperature ($T_{REG}$) by heating alone when the ambient temperature lies within a suitable range; and responsive to the reference detection signal (RD), the target detection signal (TD) and the detector temperature signal (DT) in the presence of the non-absorbing gas mixture (GMN) contained by airway, the target gas detection processor computing a temperature compensation factor (TPC) as a predetermined function of a temperature representing calibration of a non-absorbing spectral response ratio ($SRR_{NU}$) representative of a comparison of the target detection signal ($TD_{NU}$) relative to the reference detection signal ($RD_{NU}$) at an unregulated detector temperature exceeding the regulated detector temperature ($T_{REG}$) to a regulated spectral response ratio ($SRR_{NR}$) representative of a comparison of the target detection signal ($TD_{NR}$) relative to the reference detection signal ($RD_{NR}$) at the regulated detector temperature ($T_{REG}$) determined in the presence of a non-absorbing gas, wherein a spectral response ratio is a ratio of a target detector signal to a reference detector signal.

17. The method of claim 16, further comprising:

the radiation source controlling a propagation of a radiation (RAD) through an absorbing gas mixture (GMA) contained by the airway; and responsive to the reference detection signal (RD), the target detection signal (TD) and the detector temperature signal (DT) in the presence of the absorbing gas mixture (GMA) contained by airway, the target gas detection processor computing an absorbing spectral response ratio ($SRR_A$) representative of a comparison of the target detection signal ($TD_A$) relative to the reference detection signal ($RD_A$) at the unregulated detector temperature.

18. The method of claim 17, further comprising:

the target gas detection processor measuring the target gas concentration within the sample of the gas mixture (GM) as a function of the absorbing spectral response ratio ($SRR_A$) and the temperature compensation (TPC).

19. The method of claim 18, wherein the target gas detection processor measuring the target gas concentration within the sample of the gas mixture includes the target gas detection processor computing a temperature compensated spectral response ratio ($SRR_{TC}$) as a function of an application of the temperature compensation (TPC) to the absorbing spectral response ratio ($SRR_A$).

20. The method of claim 19, wherein the target gas detection processor measuring the target gas concentration within the sample of the gas mixture further includes the target gas detection processor comparing the temperature compensated spectral response ratio ($SRR_{TC}$) to the regulated spectral response ratio ($SRR_{NR}$).

* * * * *